(12) United States Patent
Myntti

(10) Patent No.: US 9,427,417 B2
(45) Date of Patent: *Aug. 30, 2016

(54) WOUND TREATMENT EMPLOYING ANTIMICROBIAL COMPOSITION

(71) Applicant: Next Science, LLC, Jacksonville, FL (US)

(72) Inventor: Matthew Franco Myntti, St. Augustine, FL (US)

(73) Assignee: Next Science, LLC, Jacksonville, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 15/075,147

(22) Filed: Mar. 19, 2016

(65) Prior Publication Data

US 2016/0199322 A1 Jul. 14, 2016

Related U.S. Application Data

(63) Continuation of application No. 13/684,456, filed on Nov. 23, 2012, now Pat. No. 9,314,017, which is a continuation of application No. PCT/US2012/059263, filed on Oct. 8, 2012.

(60) Provisional application No. 61/545,108, filed on Oct. 8, 2011, provisional application No. 61/660,649, filed on Jun. 15, 2012.

(51) Int. Cl.
| | |
|---|---|
| *A01N 25/02* | (2006.01) |
| *A01N 25/08* | (2006.01) |
| *A61K 31/14* | (2006.01) |
| *A61K 47/34* | (2006.01) |
| *A61K 47/12* | (2006.01) |

(52) U.S. Cl.
CPC ............... *A61K 31/14* (2013.01); *A61K 47/12* (2013.01); *A61K 47/34* (2013.01)

(58) Field of Classification Search
CPC ...... A01N 25/02; A01N 25/08; A01N 59/00; A01N 61/00
See application file for complete search history.

(56) References Cited

U.S. PATENT DOCUMENTS

| | | | | |
|---|---|---|---|---|
| 6,180,640 B1* | 1/2001 | Cuny | ............... | C07D 401/04 514/215 |
| 8,784,790 B2* | 7/2014 | Myntti | ............... | A61K 47/20 424/659 |
| 9,314,017 B2* | 4/2016 | Myntti | ............... | A01N 25/02 |
| 2008/0020025 A1* | 1/2008 | Giles | ............... | A61K 33/00 424/446 |
| 2010/0086576 A1* | 4/2010 | Myntti | ............... | A01N 25/30 424/405 |
| 2012/0288469 A1* | 11/2012 | Myntti | ............... | A01N 25/10 424/78.32 |
| 2013/0079407 A1* | 3/2013 | Myntti | ............... | A01N 25/30 514/556 |
| 2014/0242188 A1* | 8/2014 | Myntti | ............... | A61K 9/0014 424/605 |

* cited by examiner

*Primary Examiner* — Mina Haghighatian
(74) *Attorney, Agent, or Firm* — Zollinger & Burleson Ltd.

(57) ABSTRACT

A process for reducing bacterial colonization in or around the area of a wound includes applying to the area a gel that includes at least one PEG and an aqueous composition which has a pH of from 2 to 4, a total solute concentration of from 1.8 to 4.0 Osm/L, and from 0.9 to 1.7 g/L of at least one cationic surfactant. The aqueous composition can include a buffer system that includes an organic acid and a salt of an organic acid. The gel is effective even when free of materials having antimicrobial properties other than those provided by the aqueous composition, such as sporicides, antifungals and antibiotics.

20 Claims, No Drawings

WOUND TREATMENT EMPLOYING ANTIMICROBIAL COMPOSITION

CROSS-REFERENCE TO RELATED APPLICATIONS

This application is a continuation of U.S. patent application Ser. No. 13/684,456, filed 23 Nov. 2012 and now issued as U.S. Pat. No. 9,314,017, which is a continuation of international appl. No. PCT/US2012/059263, filed 8 Oct. 2012, which claims the benefit of U.S. patent appl. Nos. 61/545,108, filed 8 Oct. 2011, and 61/660,649, filed 15 Jun. 2012, the disclosures of all of which are incorporated herein by reference.

BACKGROUND INFORMATION

Microbes are found virtually everywhere, often in high concentrations, and are responsible for a significant amount of disease and infection. Killing and/or eliminating these microorganisms is desirable for a variety of reasons.

Bacteria present special challenges because they can exist in a number of forms (e.g., planktonic, spore and biofilm) and their self preservation mechanisms make them extremely difficult to treat and/or eradicate. For example, the bacteria in biofilms or spores are down-regulated (sessile) and not actively dividing, which makes them resistant to attack by a large group of antibiotics and antimicrobials that attack the bacteria during the active parts of their lifecycle, e.g., cell division.

In a biofilm, bacteria interact with and adhere to surfaces and form colonies which facilitate continued growth. The bacteria produce exopolysaccharide (EPS) and/or extracellular-polysaccharide (ECPS) macromolecules that keep them attached to the surface and form a protective barrier effective against many forms of attack. Protection most likely can be attributed to the small diameter of the flow channels in the matrix, which restricts the size of molecules that can reach the underlying bacteria, and consumption of biocides through interactions with portions of the EPS/ECPS macromolecular matrix and bacterial secretions and waste products contained therein. (Certain fungi also can form biofilms, many of which present the same types of challenges presented here.)

Bacteria also can form spores, which are hard, non-permeable protein/polysaccharide shells or coatings. Spores provide additional resistance to eradication efforts by preventing attack from materials that are harmful to the bacteria.

Due to the protection afforded by a macromolecular matrix (biofilm) or shell (spore) and their down-regulated state, bacteria in these states are very difficult to treat. The types of biocides and antimicrobials effective in treating bacteria in this form are strongly acidic and/or oxidizing, often involving halogen atoms, oxygen atoms, or both. Common examples include hypochlorite solutions (e.g., bleach), phenolics, mineral acids (e.g., HCl), $H_2O_2$, and the like. Large dosages of such chemicals must be allowed to contact the biofilm or spore for extended amounts of time to be effective, which makes them impractical for many applications.

Recently developed formulations intended for use in connection with compromised animal/human tissue solvate a biofilm matrix so that still-living bacteria can be rinsed or otherwise removed from infected tissue; see, e.g., U.S. Pat. Nos. 7,976,873, 7,976,875, 7,993,675, etc. The concentrations of active ingredients in these formulations are too low to effectively kill the bacteria, however, thus making such formulations ill suited for use as surface disinfectants.

Neutral-to-very acidic disinfecting solutions that can disrupt macromolecular matrices, or bypass and/or disable their inherent defenses, allowing ingredients in the solutions to access the bacteria, attack cell membranes, and kill them have been described in U.S. Pat. Publ. No. 2010/0086576 A1.

Animal tissue wounds present both a good environment for bacterial, and even biofilm, growth and a surface or substrate requiring gentle treatment, thus making a difficult problem even worse.

Dental plaque, a biofilm that adheres to a tooth surface, consists of bacterial cells (mainly *Streptococcus mutans* and *Streptococcus sanguis*), salivary polymers and bacterial extracellular products. The accumulation of microorganisms subject the teeth and gingival tissues to high concentrations of bacterial metabolites, which results in widespread problems such as gingivitis and periodontal disease, including oral caries.

Nosocomial or hospital acquired infections (HAIs) can be caused by viral, bacterial, and/or fungal pathogens and can involve any system of the body. HAIs are a leading cause of patient deaths, and they increase the length of hospitalizations for patients, mortality and healthcare costs; in the developed world, they are estimated to occur in 5-10% of all hospitalizations, even higher for pediatric and neonatal patients. They often are associated with medical devices or blood product transfusions. Three major sites of HAIs are bloodstream, respiratory tract, and urinary tract. Most patients who have HAIs have invasive supportive measures such as central intravenous lines, mechanical ventilation, and catheters, which provide an ingress point for pathogenic organisms. Ventilator-associated pneumonia can be caused by *Staphylococcus aureus*, methicillin-resistant *Staphylococcus aureus* (MRSA), *Candida albicans*, *Pseudomonas aeruginosa*, *Acinetobacter baumannii*, *Stenotrophomonas maltophilia*, *Clostridium difficile*, and Tuberculosis, while other HAIs include urinary tract infections, pneumonia, gastroenteritis, vancomycin-resistant *Enterococcus* (VRE), and Legionellosis.

Medical equipment such as endoscopes, gastroscopes, the flow-channels of hematology and dialyzer equipment, the airflow path of respiratory equipment, ISE, HPLC, and certain catheters are designed to be used multiple times. Significant risks have been associated with inadequate or improper cleaning due to the presence of residual soil and/or improper disinfection or sterilization, up to and including HAIs from contaminated devices such as broncho-scopes contaminated with *Mycobacterium tuberculosis* and the transmission of Hepatitis C virus to patients during colonoscopy procedures.

Any surface that is or becomes moist is subject to biofilm formation. Thus, articles intended for permanent or temporary implantation—such as artificial hearts, stents, contact lenses, intrauterine devices, artificial joints, dental implants—are particularly susceptible. Extreme measures are taken to prevent biofilm formation because, once established, they are essentially impossible to eradicate in vivo and can cause life-altering, even lethal, infections.

Compositions and articles that can be used in the treatment of microbes such as bacteria remain desirable. Liquids that break down the EPS/EPCS macromolecular matrix or that bypass and/or disable the defenses inherent in therein, thereby permitting the liquid or a component thereof to access and kill the bacteria in a down-regulated state, are particularly desirable. Such a liquid that is lethally effective while having no or very limited toxicity is of significant interest and commercial value.

Methods and articles capable of treating bacteria that colonize acute wounds at the time of injury and during all stages of healing, as well as in the treatment of chronic wounds, also are highly desirable.

Also of significant interest are methods, compositions capable of treating and/or remedying any of a variety of oral and mucosal conditions associated with biofilms; preventing or remedying HAIs and/or biofilms in which the microorganisms can be entrained; preventing the growth of or removing biofilms from implantable (or implanted) devices and articles; and sterilizing or otherwise processing multiuse medical equipment.

SUMMARY

The present invention is directed to compositions and articles that can be used in treatment or elimination of microbes including but not limited to bacteria, regardless of whether they are in planktonic, spore, or biofilm form.

An aqueous composition according to the present invention is lethal toward a wide spectrum of gram positive and gram negative bacteria and exhibits lethality toward other microbes such as viruses, fungi, molds, yeasts, and bacterial spores.

In addition to having a pH greater than 7, the composition includes a significant amount of one or more surfactants and large amounts of osmotically active solutes. The composition is effective at interrupting or breaking ionic crosslinks in the macromolecular matrix of a biofilm, which facilitates passage of the solutes and surfactant through the matrix to the bacteria entrained therein and/or protected thereby. These ingredients, while typically ineffective against bacteria when used in isolation or at low concentrations, become very effective at breaking down the bacterial biofilm or bypassing and disabling the bacterial biofilm defenses, allowing the bacteria in its several states to be accessed and killed (by inducing membrane leakage in bacteria, leading to cell lysis) when provided in the correct combination and in sufficient concentrations.

Articles, compositions and methods for treating wound areas also are provided. Non-solid compositions can be applied to the area; the composition can be non-flowing if it is intended to be left in place or can be a liquid if it is intended to irrigate or otherwise flow over or around a treatment area. A solid article can be applied to a wound treatment area; such an article can be adapted to be left in place on or near the treatment area or can be intended for temporary application and removal. An antihemorrhagic can be included in a composition or article to permit the composition or article to stanch bleeding, in addition to providing antimicrobial treatment. These aspects also provide methods of cleaning, dressing and otherwise treating wounds.

Also provided are articles, compositions, and methods for protecting against or treating microbial attack of the mouth, teeth, gums, lips, oral mucosal lining, particularly attack by biofilm-related conditions including, but not limited to, oral caries, gingivitis, periodontitis, halitosis, and peri-implantitis.

Further, HAIs can be prevented or remedied by applying a liquid or solid antimicrobial composition to a surface located in a medical treatment facility so as to prevent or remove a biofilm and/or kill bacterial entrained therein. A patient possessing a HAI also can be treated with an antimicrobial composition or an article including or based thereon.

Additionally, the surfaces of permanently or removably implantable objects can be treated so as to prevent biofilm formation or, after implantation, can be treated to remove biofilm on such surfaces.

Reusable medical equipment also can be processed so as to remove EPS/ECPS, materials conducive to the growth of EPS/ECPS, and organisms that are or can be entrained in EPS/ECPS. The processing can involve sterilization or can supplement existing sterilization techniques and results in medical equipment that is less likely to introduce microbes, particularly bacteria, into a patient treated therewith.

To assist in understanding the following description of various embodiments, certain definitions are provided immediately below. These are intended to apply throughout unless the surrounding text explicitly indicates a contrary intention:

"microbe" means any type of microorganism including, but not limited to, bacteria, viruses, fungi, viroids, prions, and the like;

"antimicrobial agent" means a substance having the ability to cause greater than a 90% (1 log) reduction in the number of one or more of microbes;

"active antimicrobial agent" means an antimicrobial agent that is effective only or primarily during the active parts of the lifecycle, e.g., cell division, of a microbe;

"biofilm" means a community of microbes, particularly bacteria and fungi, attached to a surface with the community members being contained in and/or protected by a self-generated macromolecular matrix;

"residence time" means the amount of time that an antimicrobial agent is allowed to contact a bacterial biofilm;

"biocompatible" means presenting no significant, long-term deleterious effects on or in a mammalian species;

"biodegradation" means transformation, via enzymatic, chemical or physical in vivo processes, of a chemical into smaller chemical species;

"antihemorrhagic" means a compound or material that inhibits bleeding by any one or more of inhibiting fibrinolysis, promoting coagulation, promoting platelet aggregation, or causing vasoconstriction;

"hospital acquired infection" means a localized or systemic infection not present, and without evidence of incubation, at the time that a patient is admitted to a health care setting, most of which become clinically evident within 48 hours of admission;

"polyelectrolyte" means a polymer with multiple mer that include an electrolyte group capable of dissociation in water;

"strong polyelectrolyte" is a polyelectrolyte whose electrolyte groups completely dissociate in water at 3≤pH≤9;

"weak polyelectrolyte" is a polyelectrolyte having a dissociation constant of from ~2 to ~10, i.e., partially dissociated at a pH in the range where a strong poly electrolyte's groups are completely dissociated; and "polyampholyte" is a polyelectrolyte with some mer including cationic electrolyte groups and other mer including anionic electrolyte groups.

Hereinthroughout, pH values are those which can be obtained from any of a variety of potentiometric techniques employing a properly calibrated electrode.

The relevant portions of any specifically referenced patent and/or published patent application are incorporated herein by reference.

DETAILED DESCRIPTION

Useful basic (caustic) liquid compositions display at least moderately high tonicity, i.e., large amounts of osmotically active solutes and a pH that is relatively high (7.5≤pH<9) or even very high (9≤pH<11). The large amount of solutes work with surfactants that are present to induce membrane leakage in bacteria, leading to cell lysis.

The composition can contain as few as three ingredients: water, the dissociation product(s) of at least one base, and at least one surfactant, each of which generally is considered to be biocompatible. The dissociation product(s) of one or more salts also can be included.

Reductions in the concentration of hydronium ions, i.e., increases in pH, generally correspond with enhanced efficacy. This effect may not be linear, i.e., the enhancement in efficacy may be asymptotic below a certain hydronium ion concentration. As long as the pH of the composition is greater than 7 and less than ~10, the basic composition generally will be considered to be biocompatible; specifically, external exposure will result in no long-term negative dermal effects.

Basicity is achieved by adding to water (or vice versa) one or more bases such as, but not limited to, alkali metal salts of weak acids including acetates, fulmates, lactates, phosphates, and glutamates; alkali metal nitrates; alkali metal hydroxides, in particular NaOH and KOH; alkali earth metal hydroxides, in particular $Mg(OH)_2$; alkali metal borates; $NH_3$; and alkali metal hypochlorites (e.g., NaClO) and bicarbonates (e.g., NaHCO3).

In certain embodiments, preference can be given to those organic compounds which are, or can be made to be, highly soluble in water. In these and/or other embodiments, preference can be given to those bases which are biocompatible. Alternatively or additionally, preference can be given to those organic acids and bases which can act to chelate the metallic cations ionic involved in crosslinking the macromolecular matrix of a biofilm.

Surfactant can be added to water before, after or at the same time as the base(s). Essentially any material having surface active properties in water can be employed, although those that bear some type of ionic charge are expected to have enhanced antimicrobial efficacy because such charges, when brought into contact with a bacteria, are believed to lead to more effective cell membrane disruption and, ultimately, to cell leakage and lysis. This type of antimicrobial process can kill even sessile bacteria because it does not involve or entail disruption of a cellular process. Potentially useful anionic surfactants include, but are not limited to, sodium chenodeoxycholate, N-lauroylsarcosine sodium salt, lithium dodecyl sulfate, 1-octanesulfonic acid sodium salt, sodium cholate hydrate, sodium deoxycholate, sodium dodecyl sulfate, sodium glycodeoxycholate, sodium lauryl sulfate, and the alkyl phosphates set forth in U.S. Pat. No. 6,610,314. Potentially useful cationic surfactants include, but are not limited to, cetylpyridinium chloride, tetradecyl-trimethylammonium borime, benzalkonium chloride, hexadecylpyridinium chloride monohydrate and hexadecyltrimethylammonium bromide, with the latter being a preferred material. Potentially useful nonionic surfactants include, but are not limited to, poly-oxyethyleneglycol dodecyl ether, N-decanoyl-N-methylglucamine, digitonin, n-dodecyl B-D-maltoside, octyl B-D-glucopyranoside, octylphenol ethoxylate, polyoxyethylene (8) isooctyl phenyl ether, polyoxyethylene sorbitan monolaurate, and polyoxyethylene (20) sorbitan mono-oleate. Useful zwitterionic surfactants include but are not limited to 3-[(3-cholamidopropyl) dimethylammonio]-2-hydroxy-1-propane sulfonate, 3-[(3-cholamidopropyl) dimethylammonio]-1-propane sulfonate, 3-(decyldimethylammonio) propanesulfonate inner salt, and N-dodecyl-N,N-dimethyl-3-ammonio-1-propanesulfonate.

For other potentially useful materials, the interested reader is directed to any of a variety of other sources including, for example, U.S. Pat. Nos. 4,107,328, 6,953,772, and 7,959,943. Particular classes and types of surfactants can be preferred for certain end use applications, with some of these being specifically referenced later in this document.

The composition contains a sufficient amount of surfactant to interrupt or rupture bacterial cell walls. The amount of surfactant constitutes greater than ~0.075%, ~0.10%, ~0.125%, ~0.15% or ~0.175%, generally at least ~0.2%, typically at least ~0.5%, more typically at least ~0.7%, often at least ~0.9%, and preferably at least 1% of the composition (all being weight percentages based on total weight of the composition), with the upper limit being defined by the solubility limits of the particular surfactant(s) chosen. Some surfactants can permit extremely high loading levels, e.g., at least 5%, at least 10%, at least 12%, at least 15%, at least 17%, at least 20%, or even on the order of ~25% or more (again, all being weight percentages based on total weight of the composition). Any of the foregoing minimum amounts can be combined with any of the foregoing maximum amounts to provide an exemplary range of potential amounts of surfactant.

Ionically charged compounds that do not qualify as a surfactants might be able to replace some or all of the surfactant component in some instances. Ionically charged compounds include natural polymers such as chitosan and glucosides, as well as charged molecules and atoms such as such as $Cl^-$, $Na^+$, $NH_4^+$, $HCO_3^-$, $SO_4^{-2}$, $HSO_4^-$, $S_2O_3^{-2}$, $SP_3^{-2}$, $OH^-$, $NO_3^-$, $ClO_4^-$, $CrO_4^{-2}$, $Cr_2O_7^{-2}$, $MnO_4^{-2}$, $PO_4^{-3}$, $HPO_4^{-2}$, $H_2PO_4^-$, and the like. These types of ions also can increase the osmolarity of a composition without increasing its pH past a desired target; see also, e.g., U.S. Pat. No. 7,090,882. Such compounds, upon dissociation, increase the effective amount of solutes in the composition without greatly impacting the molar concentration of hydroxyl ions while, in some cases, simultaneously providing a buffer system in the composition.

The lethality of the surfactant component(s) is increased and/or enhanced when the composition has at least moderate effective solute concentrations (tonicity). The osmolarity of the composition generally increases in proportion with the amount of base(s) employed, with the osmolarity maximum for a given composition primarily being a function of the solubility limits of the specific base(s). An obvious corollary to increased levels of base(s) in the composition is lower concentrations of hydronium ions, i.e., high pH values.

As noted previously, some end-use applications can call for a composition with only a moderately high pH. To increase the osmolarity of a composition without increasing its pH past a desired target, one or more types of other water soluble compounds can be included. Such compounds, upon dissociation, increase the effective amount of solutes in the composition without greatly impacting the molar concentration of hydroxyl ions while, simultaneously, providing a buffer system in the composition. The ionically charged molecules and atoms discussed above are among those materials which can serve this function; see also, e.g., U.S. Pat. No. 7,090,882.

Regardless of how achieved, the tonicity of the composition is at least moderately high, with an osmolarity of at least ~0.3, ~0.5, ~0.7, ~0.8, ~0.9 or ~1 Osm/L being preferred for most applications. Depending on particular end-use application, the composition can have any of the following concentrations: at least ~1.5 Osm/L, at least ~1.75 Osm/L, at least ~2.0 Osm/L, at least ~2.25 Osm/L, at least ~2.5 Osm/L, at least ~2.75 Osm/L, at least ~3.0 Osm/L, at least ~3.25 Osm/L, at least ~3.5 Osm/L, at least ~3.75 Osm/L, at least ~4.0 Osm/L, and even at least ~4.25 Osm/L. Certain embodiments of the composition can exhibit solute concentrations of 0.3 to 5 Osm/L, 0.5 to 4.5 Osm/L, 0.75 to 4.4 Osm/L, 1 to 4.3 Osm/L, 1.25 to 4.25 Osm/L, 1.4 to 4.1 Osm/L, and 1.5 to 4 Osm/L; other potentially useful ranges include 3 to 5 Osm/L, 2.5 to 4.5 Osm/L, 3 to 4.5 Osm/L, 3.5 to 5 Osm/L, 3.25 to 4.5 Osm/L, and the like.

The composition can be employed in a variety of ways. For example, when used to treat a biofilm on a surface (e.g., cutting board, counter, desk, etc.), the composition can be applied directly to the biofilm, optionally followed by physical rubbing or buffing, or the composition can be applied to the rubbing/buffing medium, e.g., cloth. Where a biofilm in an inaccessible area is to be treated, soaking or immersion of the biofilm in an excess of the composition can be performed for a time sufficient to essentially solvate the biofilm, which then can be flushed or wiped from the affected area. Regardless of contact method, the surfactant compo-nent(s) are believed to kill significant numbers of bacteria without a need for the bacteria to be removed from the biofilm or vice versa.

Due to the abundance of microbial contamination, the composition may find utility in a large number of potential uses including, but not limited to, household applications including non-compromised skin (hand, foot, hair, and body washing and/or deodorization), kitchen cleaning (countertop and surface cleaning, cleaning of food preparation utensils, dish washing, produce washing, etc.), bathroom cleaning (countertop and surface cleaning, fixture cleaning, toilet bowl cleaning, sink and floor drain cleaning, and shower mildew eradication), laundry area cleaning (including laundry detergent, linen disinfection, and diaper sterilization), baby sensitive applications such as cleaning and or disinfecting baby contact products (including toys, bottles, pacifiers, nipples, teething rings, diapers, blankets, and clothing); commercial applications include livestock care (facility and equipment sterilization and dairy teat dip), produce sterilization (an alternative to irradiation, which can be particularly useful against *E. coli, listeria*, salmo-nella, botulism, etc.), meat and poultry processing facilities (including all surfaces, floors and drains, processing equipment and carcass washing), commercial kitchen and food preparation facilities (countertop and surface cleaning, food preparation utensil cleaning, storage equipment and facilities cleaning, dish washing and produce washing), mass food and beverage processing (processing and storage equipment cleaning, tank sterilization, cleaning of liquid transport lines, etc.), cleaning of water lines (e.g., for drinking water, beverage dispensers, dental offices, plumbing, heat exchanging systems, and the like), and food and beverage transport (cleaning of tanker units for semi transport, cleaning of tanker cars for railroad transport, and cleaning of pipelines); and non-traditional uses such as denture cleaning, acne treatment, spermicides, laboratory equipment cleaning, laboratory surface cleaning, oil pipeline cleaning, and test article processing for biofilm attachment.

The composition can be prepared in a number of ways. Description of an exemplary method follows.

Base (e.g., NaOH) and optional solute (e.g., a phosphate or sulfate) are combined with sufficient water to constitute 60-90% of the calculated desired volume. This solution can be stirred and/or heated. The desired amount of surfactant(s) then can be added. Once stirring, if used, is complete, sufficient water is added so as to bring the composition to the calculated tonicity and pH value. Advantageously, no special conditions or containers are needed to store the composition for an extended time, although refrigeration can be used if desired.

A variety of additives and adjuvants can be included to make a composition more amenable for use in a particular end-use application without negatively affecting its efficacy in a substantial manner. Examples include, but are not limited to, emollients, fungicides, fragrances, pigments, dyes, defoamers, foaming agents, flavors, abrasives, bleaching agents, preservatives (e.g., antioxidants) and the like.

The composition does not require inclusion of an active antimicrobial agent for efficacy, but such materials can be included in certain embodiments. For example, one or more of bleach, any of a variety of phenols, aldehydes, quaternary ammonium compounds, etc., can be added.

The composition conveniently can be provided as a solution, although other forms might be desirable for certain end-use applications. Accordingly, the composition can provided as a soluble powder (for subsequent dilution, an option which can reduce transportation costs), a slurry, or a thicker form such as a gel or paste (which might be particularly useful for providing increased residence times). For the latter, the composition can include additional ingredients such as a coalescent (e.g., polyvinylpyrrolidone).

Embodiments of the composition can provide very large reductions in the number of bacteria, even with extremely short residence times. For example, a composition having high concentrations of surfactant (e.g., 1.5-2.5% by wt.) and total solutes (e.g., 2-4 Osm) can provide a 2, 3 or 4 log (99.99%) reduction in the number of bacteria in an entrenched biofilm with a 3, 4, 5, 7, 8, 9, or 10 minute residence time and a 3, 4, 5, or 6 log (99.9999%) reduction in the number of planktonic bacteria with a mere 30-second residence time.

Quantitative Carrier Testing (ASTM E2197) is designed to determine the contact time necessary to eradicate from a surface (e.g., countertops, sinks, bathroom fixtures, and the like) bacteria in a soil-loaded inoculum. In this test, bacteria combined with a soil loading and a 10 μL inoculum is placed on a stainless steel carrier disk. After the inoculate is allowed to dry completely, 50 μL of antimicrobial treatment composition is applied and allowed to stay in place for the desired treatment time, after which dilution with a saline dilution is performed.

In addition to the foregoing general uses for the caustic composition of the present invention, certain specific end uses can employ the caustic antimicrobial composition, its acidic counterpart or, in some instances, a solid antimicrobial material. The following paragraphs set forth information about an acidic antimicrobial composition and a solid antimicrobial material, as well as specific novel end uses for such compositions and materials.

Potentially useful acidic liquid compositions include those described in the aforementioned U.S. Pat. Nos. 7,976,873, 7,976,875, and 7,993,675 as well as U.S. Pat. Publ. No. 2010/0086576 A1, all of which include large amounts of osmotically active solutes. A primary difference among the liquid compositions is pH, with those intended for use in the ear or sinus cavity being very moderate (e.g., commonly about 6≤pH≤7), while those intended for surface disinfection being more extreme, e.g., relatively low (about 3≤pH≤6).

An acidic antimicrobial composition can contain as few as three ingredients: water, the dissociation product(s) of at least one acid, and at least one surfactant, each of which generally is considered to be biocompatible. The dissociation product(s) of one or more alkali metal salts of organic acids also can be included.

Increases in the concentration of hydronium ions, i.e., decreases in pH, generally correspond with enhanced efficacy and, again, the effect may not be linear, i.e., the enhancement in efficacy may be asymptotic past a certain hydronium ion concentration. As long as the pH of the composition is greater than ~3, the composition generally will be biocompatible; specifically, external exposure will result in no long-term negative dermal effects.

Acidity is achieved by adding to water (or vice versa) one or more acids, specifically strong (mineral) acids such as HCl, $H_2SO_4$, $H_3PO_4$, $HNO_3$, $H_3BO_3$, and the like or, preferably, organic acids, particularly organic polyacids. Examples of organic acids include monoprotic acids such as formic acid, acetic acid and substituted variants, propanoic acid and substituted variants (e.g., lactic acid, pyruvic acid, and the like), any of a variety of benzoic acids (e.g., mandelic acid, chloromandelic acid, salicylic acid, and the like), glucuronic acid, and the like; diprotic acids such as oxalic acid and substituted variants (including oxamic acid), butane-dioic acid and substituted variants (e.g., malic acid, aspartic acid, tartaric acid, citramalic acid, and the like), pentanedioic acid and substituted variants (e.g., glutamic acid, 2-ketoglutaric acid, and the like), hexanedioic acid and substituted variants (e.g., mucic acid), butenedioic acid (both cis and trans isomers), iminodiacetic acid, phthalic acid, ketopimelic acid, and the like; triprotic acids such as citric acid, 2-methylpropane-1,2,3-tricarboxylic acid, benzenetricarboxylic acid, nitrilotriacetic acid, and the like; tetraprotic acids such as prehnitic acid, pyromellitic acid, and the like; and even higher degree acids (e.g., penta-, hexa-, heptaprotic, etc.). Where a tri-, tetra-, or higher acid is used, one or more of the carboxyl protons can be replaced by cationic atoms or groups (e.g., alkali metal ions), which can be the same or different.

In certain embodiments, preference can be given to those organic acids which are, or can be made to be, highly soluble in water; acids that include groups that enhance solubility in water (e.g., hydroxyl groups), examples of which include tartaric acid, citric acid, and citramalic acid, can be preferred in some circumstances. In these and/or other embodiments, preference can be given to those organic acids which are biocompatible; many of the organic acids listed above are used in preparing or treating food products, personal care products, and the like. Alternatively or additionally, preference can be given to those organic acids which can act to chelate the metallic cations ionic involved in crosslinking the macromolecular matrix of a biofilm. This is discussed in more detail below.

Surfactant can be added to water before, after or at the same time as the acid(s). As with the basic antimicrobial composition, those surfactants that bear some type of ionic charge are expected to yield enhanced antimicrobial efficacy; such charges, when brought into contact with a bacterium, are believed to lead to more effective cell membrane disruption and, ultimately, to cell leakage and lysis. Potentially useful surfactants are the same as those described previously, with non-ionic and cationic surfactants being at least somewhat preferred where the composition is intended for contact with dermal tissue.

The amounts of such surfactants that can be employed in the acidic antimicrobial composition are the same as those described above in connection with the basic antimicrobial composition.

The lethality of the surfactant component(s) is increased and/or enhanced when the composition has at least moderate effective solute concentrations (tonicity). The osmolarity of the composition generally increases in proportion with the amount of acid(s) employed, with the osmolarity maximum for a given composition primarily being a function of the solubility limits of the specific acid(s). An obvious corollary to increased levels of acid(s) in the composition is higher concentrations of hydronium ions, i.e., low pH values. As noted previously, some end-use applications can call for a composition with only a moderately low pH. To increase the osmolarity of a composition without decreasing its pH past a desired target, one or more types of other water soluble compounds can be included. Such compounds, upon dissociation, increase the effective amount of solutes in the composition without greatly impacting the molar concentration of hydronium ions while, simultaneously, providing a buffer system in the composition. The materials and methods for enhancing tonicity, as well as the osmolarities of the resulting compositions, are the same as those described above in connection with the basic antimicrobial composition.

Where one or more organic acids are used in the composition, tonicity can be increased by including salt(s) of those acid(s) or other acid(s). For example, where the composition includes x moles of an acid, a many fold excess (e.g., 3×-10×, preferably at least 5× or even at least 8×) of one or more salts of that base also can be included.

Both the basic and acidic antimicrobial liquid compositions have been described primarily as solutions, although this is not limiting. Additional forms include emulsions, gels (including hydrogels, organogels and xerogels), pastes (i.e., suspension in an organic, typically fatty, base), salves or ointments, aerosols, foams, and even suspensions.

Solid articles intended for use in disinfecting applications are described in U.S. Pat. Publ. No. 2012/0288469. Solid materials include a crosslinked version of a water soluble polyelectrolyte and entrained surfactant. This combination of components permits the local chemistry within and immediately surrounding the solid material, when in use in an aqueous environment, to mimic that of the acidic versions of the aforedescribed liquid composition: high tonicity and high surfactant concentration. The solid material can, but need not, include biocidal additives, particularly active antimicrobial agents. When a liquid is passed through or in proximity to the solid material, any bacteria or other microorganisms are exposed to the local chemistry conditions discussed above: high tonicity, relatively low pH, and available surfactant, a combination that can induce membrane leakage in bacteria, leading to cell lysis. These characteristics permit the solid material to be effective at bypassing and disabling bacterial biofilm and spore defenses. In addition to being lethal toward a wide spectrum of gram positive and gram negative bacteria, the solid materials also can exhibit lethality toward other microbes such as viruses, fungi, molds, and yeasts.

The solid material requires some level of water or humidity to function effectively. This can determined or defined in a variety of ways. The polyelectrolytes must be capable of localized liquid charge interaction (meaning at least two water molecules are contacting or very near an electrolyte group); alternatively, sufficient water must be present to activate the charge of the electrolyte and/or to permit bacterial growth.

A solid antimicrobial material does not itself have a true pH. In use, however, the local pH of any aqueous composition in which it is deployed preferably is lower than ~7 to ensure proper antimicrobial activity. Reduced pH values (e.g., less than ~6.5, ~6.0, ~5.5, ~5.0, ~4.5 and even ~4.0) generally are believed to correlate with increases in efficacy of the solid material, although this effect might be asymptotic for reasons described above.

In addition to more strongly acidic local environments, high local osmolarity conditions also are believed to increase efficacy. Accordingly, larger concentrations of polyelectrolytes, larger concentrations of surfactant, surfactants with shorter chain lengths (e.g., no more than $C_{10}$, typically no more than $C_8$, commonly no more than $C_6$), and surfactants with smaller side groups around the polar group each are more desirable. (These factors also are applicable to the previously described liquid compositions.)

The lethality of the surfactant component(s) is increased and/or enhanced when the solid material can provide to the local environment in which it is deployed at least moderate effective solute concentrations, similar to that described above. Local osmolarity (tonicity) generally increases in proportion to the number and type of electrolytes present in the polymeric network. (By local osmolarity is meant that of a liquid contained in the solid material. While this might vary from place to place throughout the article, preference is given to those solid materials capable of providing high local osmolarities throughout.)

The polyelectrolyte(s) that form the bulk of the solid material preferably are at least somewhat water soluble but also essentially water insoluble after being crosslinked. A partial list of polyelectrolytes having this combination of characteristics includes, but are not limited to, strong polyelectrolytes such as polysodium styrene sulfonate and weak polyelectrolytes such as polyacrylic acid, pectin, carrageenan, any of a variety of alginates, polyvinylpyrrolidone, carboxymethylchitosan, and carboxymethylcellulose. Included in potentially useful polyamphyolytes are amino acids and betaine-type crosslinked networks; examples would be hydrogels based on sodium acrylate and trimethylmethacryloyloxyethylammonium iodide, 2-hydroxyethylmethacrylate, or 1-vinyl-3(3-sulfopropyl)imidazolium betaine. Those polymeric materials having electrolyte groups that completely (or nearly completely) dissociate in water and/or provide relatively low local pH values are desired for efficacy are preferred. Also preferred are those polyelectrolytes having a high density of mer with electrolyte-containing side groups.

Several crosslinking mechanisms including but not limited to chemical, high temperature self-crosslinking, and irradiation can be employed in forming the solid material. Another option is to create crosslinks during the polymerization process itself, such as by con-densing adjacent sulfonic acid groups to yield sulfonyl crosslinks. Solid materials with higher crosslink densities tend to maintain higher surfactant concentrations for a longer period of time due to, presumably, longer mean free paths in the polymeric network.

Independent of crosslinking method, the solid material can be formed by crosslinking polymers (or polymerizable monomers) in an aqueous solution contained in a heat conductive mold, followed by rapid freezing and subsequent lyophilizing. The resulting sponge-like material generally takes the shape of the mold in which it was formed. Solids resulting from this type of process often have a spongy appearance, with relatively large pores connected by tortuous paths. Often, pores less than ~0.22 µm, less than ~0.45 µm, less than ~0.80 µm, and less than ~0.85 µm are desirable (based on the diameters of endotoxins, bacteria, and spores); for these and other applications, a solid material with at least some larger pores (e.g., less than ~1, 2, 5, 10, 50, or 100 µm) can be used.

The solid material contains a sufficient amount of surfactant to interrupt or rupture cell walls of bacteria contacting or coming into the vicinity of the solid material. The surfactant component(s) generally constitute as low as ~0.03% and as high as ~10%, ~15% or even ~17.5% (all by wt.) of the solid material. The same types of surface active materials discussed previously also can be used in this form.

The surfactant preferably is present in the polymer network at the time that crosslinking occurs (or the time of polymerization in the case of the type of simultaneous polymerization and condensation discussed above). If it is not, a crosslinked polymer article or film must be post-treated to ensure proper entrainment of the surfactant. A possible method for accomplishing this is immersion of the article or film in a solution, typically but not always aqueous, that contains one or more surfactants, followed by removal of excess water via a drying (e.g., thermal or freeze) or evacuation process. In addition to the surfactant(s), one or more ionic compounds (salts) can be incorporated into the solid material so as to enhance its ability to create localized regions of high tonicity.

Regardless of how achieved, the local tonicity around the solid material is at least moderately high, with an osmolarity of at least ~0.1 Osm/L being preferred for most applications. Solid materials that create local tonicities greater than ~0.1 Osm/L will have enhanced bacteri-cidal activity with further increases in the osmotic pressure providing further enhanced antimicrobial efficacy.

The solid material can take any of a variety of intermediate and final shapes or forms including, but are not limited to, a spongy solid that is permeable to vapor and or liquids; a molded, extruded or deposited sheet; a coating on a surface or layer in a multilayer structure; and an extruded fiber or thread. Once in a particular shape, the material then can be further processed or manipulated so as to provide a desired shape, e.g., a sheet good can be rolled or folded so as to provide a membrane of a particular geometry or a larger solid can be ground into a powder.

Both the liquid and solid forms can act at least in part to interrupt or break ionic crosslinks in the macromolecular matrix of a biofilm, facilitating the passage of solutes and surfactant through the matrix to bacteria entrained therein and/or protected thereby. Both forms also typically do not involve $C_1$-$C_4$ alcohols, yet can result, after no more than 10 minutes residence time, in at least 6 log (99.9999%) reductions in the number of bacteria in an entrenched biofilm. Embodiments of the composition which are non-toxic if ingested can result, after no more than 10 minutes residence time, in at least 2 log (99%), 3 log (99.9%) or 4 log (99.99%) reductions in the number of bacteria in an entrenched biofilm.

In the discussion of particular applications of the previously described compositions and solid materials, terms such as "low," "moderate," and "high" are used in connection with properties such as toxicity and efficacy. Toxicity refers to negative effects on biological tissues or systems, with low toxicity referring to little or no irritation even upon repeated applications, high LD50 values, little or no cytotoxicity, and/or no systemic toxicity, and high toxicity referring to irritation upon repeated exposure, low LD50 values, and/or moderate-to-high cytotoxicity; toxicity generally increases with increasing surfactant concentration, increasing tonicity, and/or departure of pH from neutral. Efficacy refers to lethality against microbes and/or ability to disrupt or even remove the EPS/ECPS in which certain bacterial colonies reside, with low efficacy referring to <2 log, or even <1 log reduction in bacteria (particularly those in an entrenched biofilm) and high efficacy referring to >2 log, >3 log, >4 log, >5 log and even >6 log reductions in bacteria; efficacy generally increases with departures of pH from neutral, surfactant loading increases, tonicity increases, and optimization of surfactant architecture (e.g., higher charge potentials, smaller groups near a charged site, smaller hydrophilic sites, etc.) or type (i.e., cationic>zwitterionic>anionic>non-ionic).

Wounds

A number of pathogenic bacteria often are present in and around wounds. Gram positive bacteria include *Enterococcus faecalis, Staphylococcus epidermidis*, and *Staphylococcus aureus*. Gram negative bacteria include *Klebsiella pneumonia, Acinetobacter baumanii*, Haemo-philus influenza, *Burkholderia cenocepacia*, and *Pseudomonas aeruginosa*. Various fungi also can be present in burn wounds.

Wound colonization often occurs in stages, with bacterial flora in the wound changing over time. Initially, wounds are colonized by aerobic gram positive cocci, such as *S. aureus, S. epidermidis, Streptococcus* spp., and *Enterococcus* spp., followed by gram negative rods such as *P. aeruginosa, E. coli, K. pneumoniae*, and *A. baumannii*. The wound later is colonized by anaerobic species such as *Prevotella* spp., and *Porphorymonas* spp.

Bacteria can colonize a wound and form a biofilm having mixed species communities of aerobic bacteria near the surface and anaerobic bacteria deeper in the biofilm. Biofilms are a major, perhaps primary, factor in making a wound chronic and preventing healing because neither the body's natural defenses or antibiotics are able to eradicate bacteria in a biofilm. Additional reasons that wound infections can be difficult to treat include the avascular nature of wound eschars and the presence of antibiotic resistant microorganisms.

Human and animal wounds can classified as (1) acute, which includes skin abrasions, surgical incisions, trauma, and burns, or (2) chronic, which includes diabetic ulcers, pressure ulcers, and venous arterial ulcers.

Acute wounds generally heal through an orderly and timely regenerative process with sequential, yet somewhat overlapping, stages of healing: haemostasis, inflammation, and regeneration and repair.

In haemostasis, damaged endothelial lining exposes platelets to sub-endothelial collagen, which then releases von Willebrand factor and tissue thromboplastin. The von Willebrand factor facilitates platelet adhesion to sub-endothelial collagen and the adhered platelets release ADP and thromboxane A2, which leads to further platelet aggregation. Tissue thromboplastin then activates the coagulation pathways, leading to the formation of fibrin, which forms a plug into which platelets and red blood cells are trapped, thereby leading to clot formation.

In inflammation, platelets release platelet-derived growth factor and transformation growth factor β, which are chemotactic to neutrophils and monocytes. Neutrophils and macro-phages phagocytose foreign material and bacteria.

Platelet-derived growth factor and transformation growth factors are mitogenic to epithelium and fibroblasts. In the regeneration and repair phase, this leads to proliferation of epithelial cells and fibroblasts, which produce collagen. Vascular endothelial growth factor is mitogenic to endothelial cells, and it is released by monocytes in response to hypoxia and promotes angiogenesis.

During the first 24 hours of the healing process in acute wounds, neutrophils are the predominant cell type; this is the acute inflammation phase where epithelial cells start proliferating and migrating into the wound cavity. Over the next 24-48 hours, where macrophage and fibroblasts are the dominant cell types, epithelial cell proliferation and migration continues and angiogenesis begins. Granulation tissue appears and collagen fibers are present but are vertical and do not bridge the wound gap. Granulation tissue includes newly formed capillary loops.

By the end of fifth day, the predominant cell type is fibroblasts, which synthesize collagen to bridge the wound edges. Epidermal cells continue to divide, the epidermis becomes multilayered, and abundant granulation tissue is present.

During the second week, acute inflammation subsides, and collagen continues to accumulate.

The foregoing is inapplicable to burns and chronic wounds. In burn wounds, the lack of a protective barrier due to the injury often results in septic infections. In chronic wounds, the wound fails to proceed through an orderly progression, causing the wound to remain in the inflammation phase of the healing process.

The forms that the treatment can take, the stages of a wound that can benefit from a treatment, the types and forms of bacteria present in the wound, and the portions of the wound and surrounding skin that can be treated all are indicative of the breadth of the present invention. Each possible combination of variables cannot be described individually; instead, many of the variables will be discussed separately, and the ordinarily skilled artisan is capable of combining these individual descriptions to provide for a given form that can be used in or near a particular type of wound at a particular stage of the healing process.

Wound Types

Both chronic and acute wounds can affect only the epidermis and dermis or can affect tissue down to the fascia.

Chronic wounds, which primarily affect humans although also occur with horses, most often are caused by poor circulation, neuropathy, and lack of mobility, although other factors such as systemic illness (including infection and diabetes), age, repeated trauma and co-morbid ailments such as vasculitis, pyoderma gangrenosum, neoplasia, metabolic disorders, and diseases that cause ischemia (e.g., chronic fibrosis, atherosclerosis, edema, sickle cell disease, arterial insufficiency-related illnesses, etc.) or that suppress the immune system. All of these can act to overwhelm the body's ability to deal with wound damage via the common healing process be disrupting the precise balance between production and degradation of molecules such as collagen seen in acute wounds, with degradation playing a disproportionately large a role.

Many of the aforementioned causes result in inadequate tissue oxygenation, leading to a higher risk for infection. The immune response to the presence of bacteria prolongs inflammation and delays healing, leading to a chronic wound and damaged tissue. Bacterial colonization and infection damage tissue by causing a greater number of neutrophils to enter the wound site. Although neutrophils fight pathogens, they also release inflammatory cytokines and enzymes that damage cells as well as produce Reactive Oxygen Species (ROS) to kill bacteria; enzymes and ROS produced by neutrophils and other leukocytes damage cells and prevent cell proliferation and wound closure by damaging DNA, lipids, proteins, the extracellular matrix, and cytokines that facilitate healing. Neutrophils remain in chronic wounds longer than in acute wounds and contribute to the fact that chronic wounds have higher levels of inflammatory cytokines and ROS, and chronic wound fluid has an excess of proteases and ROS, so the fluid itself interferes with healing by inhibiting cell growth and breaking down growth factors and proteins in the extracellular matrix.

Chronic wounds typically are classified as diabetic ulcers, venous ulcers and pressure ulcers, although a small number of wounds not falling into one these categories can be caused by, for example, radiation poisoning or ischemia.

Generally accepted wisdom is that disinfectants are contraindicated for the treatment of chronic wounds. This belief is based on a variety of factors, including the potential to damage tissue, potential delay in wound contraction, and general ineffectiveness in the presence of organic matter, e.g., blood and exudates.

An acute wound results from a force that exceeds the resistive strength of the skin and/or underlying supporting tissues, resulting in an abrasion, puncture, laceration, or incision. Most acute wounds result from a trauma, with most of the remainder resulting from a medical procedure, e.g., surgery. Surgical wounds commonly are classified on a sliding scale that ranges from clean to contaminated to dirty, with surgical wounds that are contaminated or dirty (or known to be infected) occasionally being left open for treatment prior to being sutured. Surgical wounds almost always are dressed, with dressing selection based on the amount of exudate to be absorbed (leakage of exudate onto surrounding skin can cause blistering, particularly in the area under the dressing), supporting haemostasis and protecting against infection.

Wound Treatment

Fundamental wound care protocol involves cleansing (i.e., removal of debris and softening of necrotic tissue), possible debridement, absorbing excess exudate, promoting granulation and epithelialization, and treating infection. The cleansing agents used at this stage tend to be based on surfactants targeted at physical removal of dirt and bacteria with very little (if any) killing of bacteria being effected.

Common treatments for wounds involve dressing changes, medicated dressings, and cleansing or debridement. These often are combined with systemic and/or topical antibiotics which, unfortunately, are ineffective when treating bacteria in a biofilm due to their sessile state. (Orders of magnitude more antibiotic(s) are needed to kill bacteria in a biofilm, an amount which makes most/all antibiotics toxic to the host.)

Changing dressings to dry ones, if performed, can be a means of mechanical debridement which causes injury to new tissue growth, causes pain, predisposes a wound to infection, becomes a foreign body and delays healing time.

Debridement is performed for necrotic tissue and infection in the wound. This can be accomplished by multiple methods, including mechanical, autolytic, surgical, enzymatic or biochemical, or biological. Hydrogels are often applied to wounds to keep them hydrated. Negative pressure wound therapy can be used to pull bacteria from a wound. Hyperbaric chambers can also be used to attempt to improve wound healing.

Topical application of an antibacterial product such as alcohols, $H_2O_2$, povidone-iodine and dilute HClO, sometimes is performed to control bacterial load. A number of gels and dressing are marketed for the treatment of infections in wounds, including antibacterial silver-loaded gels, calcium fiber gels and alginates (which entrap bacteria). None of these are effective against biofilms, however, and therefore are not effective in treating many wounds.

As mentioned previously acute wounds generally heal through an orderly, multi-stage regenerative process that includes haemostasis, inflammation, and regeneration/repair. The aforementioned compositions and solid materials can be useful in treatments at each of these stages. Further, the treatments can be targeted at preventing bacterial colonization, including the formation of biofilms, or at treating an infection, including in biofilm form, in or near a wound.

Concurrent with or soon after wound formation, the wound and surrounding skin can be treated so as to minimize the risk of infection. This treatment can be effected by cleansing the area with a liquid composition or by contacting the area with a solid form carrier such as, for example, a topical wipe. At this stage, long term exposure to the treating medium is not expected, so increasing efficacy at the cost of reducing biocompatibility is acceptable.

Efficacy can be bolstered by increasing osmolarity, pushing the pH farther from neutral and/or using more aggressive surfactants. For example, liquid compositions (which includes semi-solid materials such as gels, salves and balms) intended for immediate removal or topical wipes intended for use in field situations where other treatment will not be immediate can have a relatively extreme pH (e.g., 2 to 4 or 10 to 12), whereas liquid compositions not intended for immediate removal and topical wipes intended for use in situations other than extreme situations can have an intermediate pH (e.g., 4 to 5 or 9 to 10), and liquid compositions not intended to be removed, or compositions/wipes intended for use with children or small animals, can have a gentle pH (e.g., 5 to 6.5 or 7.5 to 9).

In addition to or instead of pushing pH farther from neutral, a topical composition also can have a very high osmolarity and/or surfactant loading. Particularly because biofilms are unlikely to have formed at such an early stage, the need for $H_3O^+$ or $OH^-$ ions to assist in breaking up the EPS/ECPS macromolecular matrix might not be as great and, accordingly, higher loadings of other solutes, buffers and/or surfactants might be sufficient to provide significant lethality against many types of bacteria in planktonic form. For example, at this stage of wound care, a liquid composition with an osmolarity greater than ~300 mOsm/L and a surfactant loading greater than ~0.075% (by wt.) often can be adequate for preventing biofilm growth. Adjusting the osmolarity and/or surfactant loading upward (using the amounts provided previously) can provide more effective (i.e., biocidal) compositions, but at the cost of potential for skin irritation.

For biocompatibility reasons, non-ionic and cationic surfactants (particularly benzalkonium chloride and cetylpyridinium chloride) are preferred.

A variety of grades of liquid antimicrobial compositions for wound care also are envisioned. For example, over-the-counter (OTC) and prescription (Rx) or professional grades can be provided having compositions and properties such as those shown in the following table:

TABLE 1

Exemplary wound care compositions

| | OTC | Rx |
|---|---|---|
| Acid or base | weak acid | strong base |
| Amount of acid/base, g/L | 75-150 | 25-50 |
| Tonicity, Osm/L | 1.8-2.8 | 3.0-4.0 |
| Solute | sodium citrate dihydrate | $NaH_2PO_4$ |
| Amount of solute, g/L | 75-150 | 25-50 |
| Amount of surfactant, g/L | 0.9-1.7 | 10-20 |

Grades having intermediate properties also are envisioned.

Liquid antimicrobial compositions can be applied directly or can be delivered and continuously removed, e.g., fed via an instrument like a debrider (e.g., any of the Pulsavac Plus™ family of products, commercially available from Zimmer Inc., Warsaw, Ind.) or even a syringe with a special flow restriction (increased pressure) tip. Also, a liquid composition or one of the foregoing additional (solid or semi-solid, particularly gels including those based on any of a variety of PEGs) forms can be used to provide articles with disinfectant properties such as sponges, topical wipes, bandages, pads, gauze, surgical packing, and the like.

In addition to being applied to a wounded area to halt or prevent microbial infection, embodiments of a liquid composition (including gels and foams) or a topical wipe can be used to disinfect the skin of those treating the wound as well as the instruments used in that treatment including, but not limited to, syringes, debriders, tourniquets, and the like.

Certain types of wounds, patients and/or treatments argue for the inclusion of other types of materials in or with the disinfecting composition or material. Non-limiting examples of such materials include, but are not limited to, emollients, lotions, humectants, glycosamino-glycans such as hyaluronic acid, analgesics (e.g., pramoxine, lidocaine, capsaicin, isobutyl-propanoicphenolic acid, etc.), colloidal silver (for treatment of burns) and antimicrobials including sporicides, antifungals, antibiotics (e.g., bacitracin, neomycin, polymyxin B, etc.), fragrances, preservatives (e.g., antioxidants), and the like.

Adding an antihemorrhagic to the disinfecting (antimicrobial) composition or material, or adding the disinfectant to an antihemorrhagic, is potentially quite useful. Examples of common antihemorrhagic materials used in military and emergency medical settings include fibrin, collagen oxidized starch, carboxymethyl cellulose, thrombin and chitosan. Various embodiments of the disinfecting composition or material can be added to an antihemorrhagic material or article such as a haemostatic bandage (HemCon Medical Technologies, Inc.; Portland, Oreg.), Tisseel™ fibrin sealant (Baxter International Inc.; Deerfield, Ill.), Thrombi-Gel™ gelatin foam hemostat (Pfizer Inc.; New York, N.Y.), GelFoam™ gelatin sponge (Pfizer), GelFoam™ Plus haemostasis kit (Baxter), and the like; alternatively, addition of an antihemorrhagic material to a liquid disinfecting composition or to a solid disinfecting material or article also can be useful. For purpose of exemplification, addition of at least ~5%, often at least ~10%, commonly at least ~20% of disinfecting composition or material in solid or semisolid antihemorrhagic materials (e.g., gel-foam and chitosan bandages). Conversely, from ~1 to ~80% (by wt.), commonly from ~3 to ~70% (by wt.), and typically from ~5 to ~60% antihemorrhagic material (with the amount varying primarily based on the identity and efficacy of the antihemorrhagic, e.g., thrombin, chitosan, oxidized cellulose, or carboxymethyl cellulose) can be added to or incorporated in a disinfecting composition or material.

Embodiments of the foregoing are expected to find utility in military battlefield (e.g., pourable powders carried by field medics) and emergency medical applications (e.g., EMT and ambulance kits as well as surgical theater usages), where disinfecting capability (efficacy) preferably is high, e.g., high osmolarity and surfactant levels. Blood and wound fluid can hydrate a solid material or a concentrated liquid composition, so levels of water or other carrier can be kept low.

Other embodiments are expected to find utility in connection with less traumatic wounds, such as shaving cuts or improperly trimmed animal nails, where an embodiment of the liquid or solid disinfecting material might be added to a styptic such as alum or TiO2.

From the foregoing, the ordinarily skilled artisan can envision numerous articles, techniques and ways in which wounds can be cleansed.

Embodiments of the previously described liquid compositions and solid materials also can be used at during various stages of the wound healing process.

As described in more detail above, wounds are believed to heal via a process that involves haemostasis, inflammation, and repair and/or regeneration. During these phases, a variety of topical medicaments and articles are applied to wounds and surrounding areas, some for brief periods of time and others for an extended duration.

For example, many wounds are bandaged soon after occurrence and, in certain circumstances, re-bandaged over time. A bandage that includes an embodiment of the liquid composition can help to prevent infection, treat infection, prevent biofilms, or break up a biofilm and kill the bacteria entrained therein. In this particular form, a strong disinfecting composition (high osmolarity and relatively extreme pH, e.g., ~3.5 to 5 or ~9 to 10.5) can be preferable because high efficacy and microbial toxicity are desired and because the bandage typically only overlays the wound. Methods of making such a bandage include soaking bandage material in a liquid composition or by coating or entraining in the bandage material a gel, optionally one that undergoes a temperature-based phase change, i.e., becomes less viscous between ~25° to ~40° C. (Alternatively, some PEG-based gels themselves can act as bandages.) Tailoring the elution rate of the disinfecting composition over the expected use period of the bandage can be desirable.

Alternatively, an embodiment of a solid form disinfectant can be used to provide a bandage. The solid article can be in as-made form (e.g., spongy solid) or in further processed form (e.g., a fiber made from a solid). Here, the bandage material itself is antimicrobial, although such a material certainly can be further loaded with additional composition or with other antimicrobials.

A variation on the foregoing theme involves surgical packing, which is structurally similar to a bandage although typically is intended for insertion into the body for a limited time or to be bioresorbed within a predetermined amount of time. The method of making a surgical packing is essentially the same as those set out above with respect to bandages, although the efficacy and toxicity levels and/or the elution rate can be downwardly adjusted.

Ongoing wound treatment sometimes involve repeated applications of a gel, paste or salve directly to the wound. Because of the amount of time that such materials are allowed to reside on or in the wound, these materials typically involve gentle or only moderately strong disinfecting composition embodiments. In other words, efficacy and toxicity can be reduced to avoid pain or tissue damage, a sacrifice that is offset by the proximity of the treatment to the wound and its length of contact.

Both bandages and topical treatments can be used in connection with burn wounds. In such circumstances, addition of a variety of adjuvants and additional treatments can be preferable. Potentially useful adjuvants include colloidal silver, analgesics, antifungals, emollients, hyaluronic acid, and the like. Because wound edema is common, a somewhat concentrated, even solid, form of topically applied disinfectant can be used.

Similarly, both bandages and topical treatments can be used in connection with diabetic and pressure ulcers, i.e., chronic wounds. Similar adjuvants, particularly analgesics, hyaluronic acid, and emollients, can be included in embodiments intended for this use.

Embodiments of the liquid composition also can find utility in connection with debridement techniques and equipment. Specifically, such liquid compositions can be used to irrigate or flush an area prior to, simultaneously with, or immediately after debridement.

While most of the foregoing embodiments have been described as single use, articles intended for multiple applications are envisioned. These are expected to have high loading levels that are intended to elute over time.

Oral Care

The oral environment initially changes due to an increased concentration of carbohydrates in the diet of the host. The anaerobic bacteria in the plaque biofilm product acid by fermenting these carbohydrates, thus reducing the pH of the biofilm; some of the more common bacteria responsible for this shift in composition include *S. mutans, S. sorbrinus*, and *Lactobacillus casei*, all of which can survive at a pH level as low as 3.0. As the pH drops, the microflora shift towards acid-tolerant bacteria, as intolerant bacteria cannot survive in the acidic conditions formed.

At highly acidic pH, the acid-tolerant bacterial biofilm can de-mineralize the tooth enamel, with greater degrees of acidity causing faster rates of demineralization. (Demineralization of tooth enamel can also occur solely from the presence of highly acidic substances in the oral cavity.) Caries result if demineralization persists at a rate greater than re-mineralization occurs. *S. mutans, Lactobacilli, Lactobacillus acidophilus, Actinomyces viscosus, Nocardia* spp., and *Streptococcus sanguis* are most closely associated with oral caries but, because most plaque-induced oral diseases occur with a diverse microflora present, the specific causal species is not known.

Plaque and tartar (hardened plaque) become more harmful the longer that they remain on the teeth. The bacteria within the biofilm cause inflammation of the gums, commonly known as gingivitis, a mild form of gum disease that does not include any loss of bone and tissue holding the teeth in place. *Spirochetes, Actinomyces naeslundii*, and *P. gingivalis* are often associated with the gingivitis.

Untreated gingivitis progresses to inflammation around the tooth, commonly known as periodontitis, a condition where the gums retract from the teeth and form gaps or pockets that can become infected because they are easily colonized by microbes due to dentinal tubules and enamel fissures that lead directly into the gums; the biofilm plaque spreads and grows below the gum line. The majority of the bacteria within the microflora in these gum pockets are gram-negative anaerobes, although the identity of the microbes in the biofilm change as the biofilm itself changes. At a certain point, the organisms must disperse to other locations in the oral cavity to ensure survival.

Periodontitis involves progressive loss of the alveolar bone around the teeth and the connective tissue that holds the teeth in place due to the bacterial toxins in the biofilm and the body's immune response to the biofilm. If left untreated, this can lead to loosening and subsequent loss of teeth. The areas around and under the gums are difficult to reach via typical oral health care mechanisms that are mechanical in nature and, as such, the diseased states of gingivitis or periodontitis occur. The same bacteria listed above in connection with gingivitis can be involved in periodontitis, but an enormous variety of other bacteria can be found in these biofilms.

Peri-implantitis, which is similar to periodontitis but occurs on the surface of dental implants, refers to the destruction of the supporting peri-implant tissue due to a microbial infection. These infections tend to occur around residual teeth or failing implants, which can act as reservoirs for bacteria and form biofilm colonies, as they have no inherent host response to fight the infecting organisms. The bacterial species involved in peri-implantitis are similar to those involved in periodontitis.

The primary treatment for dental diseases is prevention. For the consumer, this involves tasks such as tooth brushing (mechanical debridement), usually with a fluoride-containing toothpaste; oral rinsing with a mouthwash containing cetylpyridinium chloride, stannous fluoride, or a combination of eucalyptol, menthol, methyl salicylate and thymol in an alcohol vehicle; and flossing. (Mouthwashes and rinses are not particularly effective at removing plaque, which necessitates continued use of floss in the inter-dental regions, as plaque tends to accumulate in these areas which brushing does not clean.) Regardless, because these preventive treatments are not effective at removing and disinfecting a biofilm, regular prophy-lactic treatment (removal of biofilm from the teeth, typically by mechanical scraping, although lasers have been used additionally or alternatively) by a dental professional usually is necessary.

When dental disease has progressed to periodontitis, mechanical scraping (debridement) has been the only way to remove a biofilm. Professional treatment by a dental professional is performed by scaling (scraping of tartar from above and below the gum line) and root planning (removal of rough spots on the tooth root where the biofilm gathers), sometimes in combination with a laser. In more serious cases, to remove more tartar, flap surgery may be performed, where the gums are lifted so that tartar can be removed, followed by suturing. Bone and tissue grafts may also be performed in the area of bone loss.

Medications are sometimes used in conjunction with mechanical treatments. These include prescription antimicrobial mouth rinses containing chlorhexidine; gum pocket inserts such as an antiseptic chip containing chlorhexidine, an antibiotic gel containing doxycycline, antibiotic microspheres containing minocycline, etc.; tablets containing doxycycline; or even systemic antibiotics.

The aforedescribed antimicrobial compositions, both acidic and caustic, can be incorporated into any of a variety of oral care vehicles such as, but not limited to oral rinses and washes intended for preventive use, oral rinses intended to treat existing dental and gum disease, oral rinse treatment after dental implants, dental implant sterilization solutions (pre-surgical), disinfecting solutions for orthodontic devices (e.g., braces, retainers, etc.), irrigation solutions (both for use in surgical procedures, such as root canals and impacted teeth prior to closure, as well as in general and localized dental procedures), and the like. The vehicle can be a liquid, gel (e.g., a sealing or packing gel used during and/or after oral surgery), paste (e.g., toothpaste), or salve (e.g., topical treatment for mouth and lip conditions such as canker sores) and can be used with components such as fluoride ions and antibiotics, if desired.

Where a liquid antimicrobial composition is to be introduced directly into an oral cavity (e.g., a mouthwash or rinse), some preference can be given to caustic compositions. Because most mouths naturally are a somewhat acidic environment, dental plaque, tartar and other forms of EPS/ECPS seem to be more impervious or resistant to chelation by acids than many other types of biofilm EPS/ECPS. Exemplary pH ranges for caustic compositions used here range from ~7.5 to ~10, commonly from ~7.7 to ~9.8, more commonly from ~7.8 to ~9.7, and typically ~9±0.5 pH units. This basicity preferably is achieved with a strong inorganic base such as KOH or NaOH.

With respect to tonicity, preferred ranges center around ~1.75 Osm/L, commonly from ~1.25 to ~2.5 Osm/L, more commonly from ~1.33 to ~2.25 Osm/L, and typically from ~1.5 to ~2 Osm/L. To reach this type of tonicity without the pH going outside the previously noted ranges, one or more ionic compounds can be included in the composition. Exemplary materials include, but are not limited to, $NaHSO_4$, $NaH_2PO_4$, NaCl, KCl, KI and the like.

Non-ionic and cationic surfactants are preferred for the same reasons set forth above in connection with wound care. Both benzalkonium chloride and cetylpyridinium chloride are known to be safe for oral applications. Exemplary surfactant loading levels range from ~0.5 to ~1.8 g/L, commonly from ~0.6 to ~1.7 g/L, and typically from ~0.75 to ~1.5 g/L.

The following table provides the composition and properties of a non-limiting example of a liquid antimicrobial composition intended for oral care applications.

TABLE 2

| Exemplary oral care composition | |
|---|---|
| pH | 9.0 ± 0.3 |
| base | NaOH |
| additional solute | $NaH_2PO_4$ |
| tonicity, Osm/L | 1750 ± 75 |
| cationic surfactant(s), g/L | 1.1 ± 0.3 |
| additives | sweetener, essential oil |

The antimicrobial compositions also can be incorporated into solid forms, such as chewing gums, lozenges, denture cleaning tablets, breath mints, removable or dissolving strips, powders and the like. They also can be used as, or incorporated in, liquids intended for aerosolizing or other spray techniques, such as breath sprays and dog teeth cleaning solutions.

For additional information on the type and amounts that can be employed exemplary liquid and solid formulations, as well as methods of making, the interested reader is directed to any of a variety of references including, for example, U.S. Pat. Publ. Nos. 2005/0169852, 2006/0210491, 2007/0166242, 2008/0286213, 2009/0252690, and 2010/0330000. Those treatments intended for preventive applications typically will be form-ulated around lower toxicity thresholds than those intended for use by dental professionals.

Adjuvants that can be included in such treating compositions include, but are not limited to, bleaching agents, binders, flavorings (e.g., essential oils and artificial sweeteners), humectants, foaming agents, abrasives, desensitizers, tooth whiteners, and analgesics.

Treatment of adenoids and tonsils, although not strictly oral care, also is possible.

Acute infections of the tonsils and adenoids generally are treated with systemic antibiotics. If tonsillitis is caused by group A *streptococcus*, penicillin or amoxicillin are commonly used with some success, while cephalosporins and macrolides being used less frequently. If these fail against β lactamase-producing bacteria (which reside in tonsil tissues and can shield group A *streptococcus* from penicillin-type antibiotics), clindamycin or amoxicillin-clavulanate may be used.

Group A β-hemolytic *streptococcus* (GABHS) is the most common reason for chronic tonsil infections. Systemic antibiotics fail to treat GABHS due to a number of factors, including the presence of β lactamase-producing organisms that protect GABHS from peni-cillins, coaggregation with *M. catarrhalis*, absence of competing bacterial flora, poor penetration of antibiotics into tonsil cells, etc. Additionally, GABHS is known to form biofilms. This bacteria, as well as other pathogenic strains, can form biofilms on and within the tonsils and/or adenoids. Infectious bacteria in biofilm form are relatively impervious to systemic antibiotics, meaning that such high levels of antibiotics are necessary to treat them (i.e., orders of magnitude more than is necessary to kill planktonic bacteria) that the patient is unlikely to survive. Biofilm infections often become chronic.

When the condition becomes chronic, surgical methods are employed to remove the tonsils and adenoids. The current treatment for chronic infections of the tonsils and adenoids is surgical removal through a tonsillectomy and adenoidectomy. This can be done by powered ablation which essentially burns away the tonsils and/or adenoids, a technique that minimizes or prevents bleeding of the tonsil bed post-surgery, or by cold steel instruments or mechanical debridement, in which case localized cauterization is performed on bleeding vessels to prevent re-bleeding after surgery. Tonsillectomy, with or without adenoidectomy, is one of the most common surgical procedures in the developed world. These surgical interventions are not without risk, however, with post-operative bleeding, airway obstruction, and adverse reaction to anesthesia being three of the most common problems. A substantial amount of pain and hospital recovery times also can be associated with these procedures. Bleeding can occur when scabs begin sloughing off from the surgical sites, generally 7 to 11 days after surgery. This occurs at a rate of about 1% to 2%, with both risk and severity being higher in adults than in children.

A topical treatment for these infections is not available, as no commercially available product can disinfect and remove the biofilm and EPS from the tonsil/adenoid surface, nor can these products penetrate into the tonsil and adenoid surface to treat bacteria within the tissue. Of the oral mouth rinses on the market, which have active ingredients that include chlorhexidine, cetylpyridinium chloride, SnF2 and mixtures of therapeutic oils, none can disinfect a biofilm in the short treatment times available in the oral cavity.

Antimicrobial compositions of the type described above, however, can be effective in treating infected adenoids and tonsils. A treatment regimen might be to gargle or rinse with up to 100 mL from 1 to 4 times each day, with the treatment running for as long as necessary, generally from 5-70 days, commonly from 7-65 days, more commonly from 8-60 days, and typically from 10-50 days, with 30±10 days being envisioned as most typical. In addition, direct application of an antimicrobial solid material directly to the affected area(s) also is envisioned.

Advantages of this type of treatment include, but are not limited to, elimination of post-operative bleeding, avoidance of anesthesia, elimination of post-operative pain, preservation of anatomy, elimination of the risks of morbidity/mortality due to surgery and post-surgical complications, and overall lower healthcare costs.

Medical Equipment

Prior to disinfection or sterilization, all reusable medical devices must be cleaned thoroughly, a step that requires that all surfaces, internal and external, be made completely free of so-called bioburden, i.e., residual body tissue and fluids, bacteria, fungi, viruses, proteins, and carbohydrates. After the manual and/or mechanical cleaning, the devices must be thoroughly rinsed to remove all residual bioburden and detergent. With current technology, if the device is not clean, sterilization cannot be achieved.

Current chemical treatments are ineffective at treating biofilms because of their inherent resistance to biocides. Biofilms can be removed by physical methods such as ultra-sound and mechanical cleaning reasonably effectively, but ensuring that it occurs correctly and completely each time is very difficult.

Endoscopes are particularly susceptible to biofilm formation due to their use within the body. Removal of biofilm from the internal surfaces of small diameter tubing within endoscopes is difficult due to limited access and the degradation of these surfaces. Biofilm formation within endoscope channels can result in failure of disinfection procedures and can create a vicious cycle of growth, disinfection, partial killing or inhibition and regrowth, and patients who undergo endoscopy with a biofilm-containing endoscope are at risk for an endoscopy related infection. Bacteria in a biofilm have been shown to be capable of surviving in a down-regulated state after being cleaned and disinfected by present methods.

The cleaning and disinfecting processes used are dependent upon the training and diligence of the operator and, while guidelines for endoscope disinfection have been developed by many organizations, no method to determine the efficacy of these regimes on a routine basis is currently available. Failure to completely clean and dry an endoscope using the current guidelines can lead to biofilm formation, with studies suggesting that human error is a major contributing factor, along with the need for rapid turnover of equipment and inadequate training.

Similar problems are inherent in the cleaning and disinfection processes used with other medical devices and equipment, although endoscopes seem to be linked to more outbreaks of HAIs, a problem discussed in more detail below.

Also problematic are devices and equipment that are not necessarily designed for invasive insertion. This includes manual instruments, powered surgical instruments, and even devices cages and guides for performing spinal surgery. These too are cleaned and disinfected post-usage, with the procedure generally involving wiping followed by sterilization (normally by steam, but occasionally by peroxide or other high performance procedures). Some devices are returned to their manufacturer for reprocessing, often with steam sterilization both before and after reprocessing.

The formulation of reprocessing cleaning solutions are unique; however, most contain some combination of at least six components: water, detergent, surfactant, buffer, and chelating agents. Enzymes are also used to increase cleaning efficacy, speed the cleaning process and help to minimize the need for manual brushing and scrubbing. A variety of enzymes, each targeting a particular type of soil, are employed, with the most common being protease (which helps to break down protein-based soils such as blood and feces), amylase (which breaks down starches like those found in muscle tissue), cellulase (which breaks down carbohydrates like those found in connective fluid and joint tissue), and lipase (which breaks down fats like those found in adipose tissue). Any combination of these enzymes may be present in a solution. Solutions containing enzymes can often be used at a more neutral pH and at lower temperatures than those without enzymes.

Enzymatic cleaning agents are used as the first step in medical device disinfection to remove biofilms. However, physical cleaning with an enzymatic cleaning agent does not disinfect the device. Even a few viable organisms that might remain after cleaning can accumulate into a biofilm over time. It has been found that commonly used enzymatic cleaners fail to reduce the viable bacterial load or remove the bacterial EPS. Cleaners with high enzyme activity remove some biofilm but fail to reduce bacterial numbers more than 2 logs (i.e., 99%), and some enzymatic solutions actually can contribute to the formation of biofilms. Accordingly, proper disinfection is required to kill down-regulated microbes and prevents the formation of biofilm.

All devices undergo a disinfection process and users perform a chemical disinfection process following cleaning. Either an oxidative or aldehyde-based chemistry is used. However, some disinfection chemistries have demonstrated a tendency to promote the formation of biofilms and none completely remove a biofilm that has already formed. Gluteraldehyde solution buildup over several uses actually has been found to promote formation of biofilms within the lumens of endoscopes.

Disinfectants employing oxidative chemistries are more effective at controlling the formation of biofilms. However, it has been found that even the harsh environment created by some disinfectants can be survived by these well-protected microbes, which can survive by using several food sources not typically thought to be possible. These disinfectants are also susceptible to deactivation by proteins that may be present on the endoscopes and medical devices, especially if the cleaning step is not adequately performed.

Cleaning chemicals require unimpeded contact with all surfaces of the device, internal and external, to assure microbial inactivation; any residuals left on the device, including medical soil, contaminants and detergent residue can interfere with that direct contact. Further, even if they have access to a biofilm, they cannot kill bacteria entrained therein.

The shape and design of some devices and instruments make it impossible to remove all of the proteins and EPS/ECPS which may be on them. Presently available cleaners or disinfection techniques are unable to completely remove EPS/ECPS, especially if there is protein which can prevent cleaning chemicals from reaching these areas. Remaining EPS/ECPS can allow for rapid biofilm reformation on the device, and the EPS/ECPS can be dislodged into the surgical field, including into the patient, allowing for a nidus of infection.

Advantageously, antimicrobial compositions of the type described above can be effective in cleaning, disinfecting and sterilizing reusable medical equipment. In these techniques, both toxicity and efficacy can be pushed to extremely high levels.

Depending on the nature of the materials from which the equipment is made, either acidic or basic compositions can be preferred. For example, a caustic composition might be preferred for a metallic piece of equipment, while an acidic composition might be preferred for a plastic piece. Extremely acidic or caustic compositions preferably are avoided, i.e., the composition employed commonly has a pH within 4 units, preferably within 3 units, and more preferably within 2 units of neutral.

Where an acidic composition is employed, a conjugate base of the acid preferably also is present. Tonicities of solutions employed here generally are at least ~2.0 Osm/L, commonly at least ~2.5 Osm/L, more commonly at least ~3.0 Osm/L, and typically at least ~3.5 Osm/L. In both acidic and caustic compositions, additional solute(s) can be present. In compositions with moderate pH (i.e., $5 \leq pH \leq 9$, particularly $6 \leq pH \leq 8$), large amounts of such solutes can be used; for example, for a composition of $6.5 \leq pH \leq 7.5$, the amount of accompanying salt or solute can be as high as 200 g/L, 250 g/L, 300 g/L, 350 g/L, 400 g/L, 450 g/L or even 500 g/L.

Regardless of the nature of the material, cationic surfactants are strongly preferred, with particular preference being given to tetradecyltrimethylammonium halides. Surfactant loading can be pushed to very high levels, e.g., 10 g/L, 15 g/L, 20 g/L, or even 30 g/L or more can be used.

Advantageously, the equipment need stay in the composition for no more than a few hours. For example, in no case should static dwell time be required to exceed 250 minutes, with less than 200 minutes being common, less than 150 minutes being more common, less than 100 minutes being even more common, and less than 50 minutes being typical. Depending on the particular antimicrobial composition employed, the dwell time can range from 1 to ~30 minutes, from ~2 to ~25 minutes, from ~3 to ~20 minutes, or from ~5 to ~15 minutes. The amount of dwell time can be decreased even more with flow for treatment and/or mechanical scrubbing to remove the EPS. Higher-than-ambient temperatures and pressures also can increase efficacy, which can be particularly useful equipment having high loadings of bioburden and/or difficult geometry (e.g., scopes).

As an example of the extreme efficacy of the liquid antimicrobial compositions described herein in this application, a citric acid/sodium citrate dihydrate composition having a pH of ~6.5 and a tonicity of ~3.5 Osm/L and including ~15 g/L tetradecyltrimethylammonium chloride surfactant was able to achieve a 9 log reduction (i.e., 99.9999999%) in *Pseudomonas* in small diameter silicone and polyethylene tubing as well as on metal and plastic coupons.

HAI

Basic routes of infection involve transmission via contact (direct and indirect), droplets, airborne, common vehicle (contaminated items such as food, water, medications, devices, and equipment), and vector (from mosquitoes, flies, rodents, etc.), with direct contact being the most frequent mode.

In direct contact, a colonized person (e.g., a caregiver or another patient) transfers the microorganism from his body to that of a susceptible patient. Indirect transmission involves contact between the host, usually a caregiver, and a contaminated object which then becomes the vector for infecting the susceptible patient; examples of objects that can become contaminated include instruments and equipment such as needles, dressings, disposable gloves, saline flush syringes, vials, bags, blood pressure cuffs, stethoscopes, and the like, as well as non-medical surfaces such as door handles, packaging, mops, linens, pens, keyboards, telephones, bed rails, call buttons, touch plates, seating surfaces, light switches, grab rails, intravenous poles, dispensers, dressing trolleys, countertops, tabletops, and the like.

Droplet transmission occurs when droplets containing microbes from an infected person are propelled a short distance through the air and deposited on the patient's body. Droplets may be produced from the source person by coughing, sneezing, talking, and during the performance of certain procedures such as bronchoscopy.

Airborne transmission can be by either airborne droplet nuclei of evaporated droplets containing microorganisms that remain suspended in the air for long periods of time or dust particles containing the infectious agent. Microorganisms carried in this manner can be dispersed widely by air currents and may become inhaled by a susceptible host in the same room as or quite remote from the original source. Microorganisms commonly transmitted in this manner include *Legionella, Mycobacterium tuberculosis* and the *rubeola* and *varicella* viruses.

Of particular and growing interest and concern are MRSA and VRE. Contamination of the environment with MRSA or VRE occurs when infected or colonized individuals are present in hospital rooms, often medical personnel carrying the organism in or on their clothing. MRSA contamination of gloves also has been observed in many personnel who had no direct contact with the patient but who had touched surfaces in infected patient's rooms. The hands, gloved or otherwise, of healthcare workers can become contaminated by touching surfaces in the vicinity of an infected patient.

In undried form, MRSA can survive for up to 48 hours on a plastic surface; in dried form, it can survive for several weeks. It is stable at a wide range of temperatures and humidities, and can survive exposure to sunlight and desiccation.

Once a surface becomes contaminated, pathogens can be transferred to other surfaces and patients in the vicinity. Hand washing and gloves can help prevent the spread of HAIs via hand-surface transmission but cannot eradicate surface or indwelling contamination, nor do they eliminate the potential for direct transfer by the patient. However, these methods do nothing to treat the presence of these pathogenic bacteria on surfaces and indwelling devices. Touch surfaces commonly found in hospital rooms often are contaminated with MRSA and VRE, with objects in closest proximity to patients having the highest levels of contamination.

The efficacy of traditional cleaning products (e.g., alcohols, quaternary ammonia compounds, and bleach) to remove surface contamination is limited. One recent study of contamination in the hospital environment detected MRSA on 74% of swab samples prior to cleaning and on 66% of swab samples after cleaning, indicating that current methods for disinfecting hospital surfaces are ineffective.

Some modern sanitizing methods are more effective against select pathogens; for example, non-flammable alcohol vapor in $CO_2$ has been demonstrated to be effective against gastroenteritis, MRSA, and influenza, while $H_2O_2$, as a liquid or vapor, has been shown to reduce infection rates and risk of acquisition, particularly in connection with endospore-forming bacteria such as *Clostridium difficile*.

However, these are so-called "contained" methods (i.e., done in a closed, controlled environment) and cannot be performed unless the object can be removed and taken to a separate treatment facility, and, even then, none have proven to be effective against biofilms and, even in those instances when sanitization is achieved, the biofilm EPS is not removed by any of these treatments (thereby permitting much more rapid re-growth of the bacterial biofilm as compared to an EPS-free surface when a pathogen is re-introduced).

From the foregoing, the ordinarily skilled artisan can envision many potential applications for the antimicrobial compositions described previously in the battle against HAIs, as well as biofilms containing or capable of entraining HAI-causing microorganisms. Common examples include cleaning and/or disinfection of any of the types of hard surfaces mentioned above, as well as floors and walls; water transport articles including sinks, therapeutic tubs, showers and drains; beds; transport devices such as gurneys and wheelchairs; surgical suites; and the like. In these instances, high efficacy and low toxicity generally are preferred. Particularly preferred are those compositions which will not harm (e.g., warp or discolor) the surface being treated.

Other common examples include cleaning and/or disinfection of any of the types of medical equipment mentioned above, particularly those which are intended for insertion into a patient (e.g., respiratory tubes, IV lines, and catheters) or application to the skin (e.g., stethoscopes, blood pressure cuffs, and the like). Again, high efficacy and low toxicity generally are preferred for this type of application.

Other examples include laundering compositions for linens and clothing, hand disinfectants and washes, surgical site preparation solutions, and the like. Laundering compositions are envisioned as typically being caustic and including high loading levels of surfactant, as well as being capable of being provided in either liquid or solid form for addition to wash water. Hand washes and surgical preparation compositions would be very similar to the OTC and Rx wound washes described previously.

No particular limitation on the types of microbes that can be treated are envisioned, with particularly problematic pathogenic organisms like *Clostridium difficile, Pseudomonas aeruginosa, Candida albicans*, MRSA, and VRE being specifically envisioned. Also envisioned is any microbe that forms or can reside in a biofilm, with treatment involving both destruction/removal of the biofilm as well as killing of the microbes entrained therein.

Implants

Although terminally sterilized, medical device implants can become colonized, prior to and during implantation, with bacteria from the environment, from a healthcare worker, or more commonly from bacteria present on the patient's own skin. After insertion, implants can become colonized from systemic bacteria which make their way to the implant which provides a surface for biofilm growth because the implant surface is not protected by the host immune defenses.

In addition, currently employed sterilization techniques are not designed to remove EPS/ECPS. Therefore, even a sterilized device/article that is properly implanted can have EPS/ECPS on its surface from previous exposure. The presence of EPS/ECPS greatly facilitates formation of a biofilm.

Soon after a device or article is implanted, a conditioning layer composed of host-derived adhesins (including fibrinogen, fibronectin, and collagen) forms on the surface of the implant and invites adherence of free-floating (planktonic) organisms. Bacterial cell division, recruitment of additional planktonic organisms, and secretion of bacterial products (such as the glycocalyx) follow, resulting in a three-dimensional structure of biofilm that contains complex communities of tightly attached (sessile) bacteria. These bacteria display cell-to-cell signaling and exist within a polymer matrix containing fluid channels that allow for the flow of nutrients and waste.

Once a biofilm forms on an implant, no currently available treatment can eradicate it. Systemic antibiotics are ineffective against such infections, certainly due to the inherent protection by the EPS/ECPS but also perhaps due to limited blood supply at the surface of the implanted article.

Most implants infected by *S. aureus* or *candida* require surgical removal. Infections with less virulent coagulase-negative staphylococci may not require surgery to remove the implant. If a decision is made to remove the infected implant, complete extraction of all components is performed, regardless of the type of infecting organism.

An infected joint prosthesis can be retained after debridement or, more commonly, removed. In removal situations, the affected area is treated with large doses of antibiotics, optionally followed by insertion of a new device either immediately or, more commonly, after a 35-45 day course of a systemic antibiotic. Infections (and treatments) associated with orthopedic devices often result in serious disabilities.

Infections associated with surgical implants are particularly difficult to manage because they require longer periods of antibiotic therapy and repeated surgical procedures. Mortality attributable to such infections is highest among patients with cardiovascular implants, particularly prosthetic heart valves and aortic grafts.

A biofilm-fouled pacemaker-defibrillator implant often is treated by a combined medical and surgical treatment. Surgical treatment is done in two-stages: the entire implanted system, including the cardiac leads, is completely removed, even in patients with clinical infection of only the pocket, because their cardiac leads may already be colonized (with cardiac rhythm being controlled by a temporary mechanism), a lengthy course of systemic antibiotics is administered (up to two weeks for infections of the pulse-generator pocket or 35-45 days for lead-associated endocarditis), and a replacement device/article is implanted on the contralateral side of the patient.

Infections of fracture-fixation devices that involve bone are treated with a 6-week course of systemic antibiotics, whereas 10 to 14 days of antibiotic therapy are sufficient for superficial infections. Infection of intramedullary nails is often associated with nonunion of bone and requires removal of the infected nail, insertion of external-fixation pins, and if necessary, subsequent insertion of a replacement nail. Surgical treatment of infection of external-fixation pins usually consists of a single procedure to remove the infected pins and, if bone union has not occurred, either insert new pins at a distant site or fuse the bones.

Treatment of infected mammary implants usually entails a two-stage replacement procedure: removal of the infected implant and debridement of the capsule surrounding it. After administration of a course of systemic antibiotics and time for the area to heal somewhat, the contralateral implant is removed, and a replacement pair of mammary implants is inserted.

An infected penile implant typically is removed, and a malleable penile prosthesis is inserted to preserve space.

After the necessary systemic antibiotic treatment, a new inflatable implant is inserted in place of the malleable prosthesis.

Even cutaneous implants such as tracheotomy tubes, ostomy bags, catheters, and piercings can become fouled with biofilms that are difficult to remove, a problem exacerbated by the non-removal nature of certain types of these articles.

The aforedescribed antimicrobial compositions can be effective topical treatments, applied to a to-be-implanted device or article or can be used to wash the infected implant and surrounding tissue to rid the body of a biofilm and/or biofilm-forming materials such as EPS/ECPS. The types of surfaces involved can be or include PTFE, PVC, silicone gels and rubbers, polyethylene, polypropylene, poly(meth)acrylates, stainless steel, precious metals (e.g., gold, silver, and platinum), ceramics, and titanium.

The pocket where the implant is or was located likewise can be treated with a liquid composition of the types mentioned above in connection with wound care. This can be done at the time of the original implantation (i.e., immediately following insertion of the article and prior to suturing), and can be followed with rinsing/irrigation, suctioning or both.

For implants in contact with body tissue, low toxicity but moderate-to-high efficacy is desired; this might be achievable with a composition having a fairly neutral pH (e.g., pH 9) but moderate-to-high osmolarity, e.g., at least ~1.5 Osm/L, commonly at least ~1.75 Osm/L, more commonly at least ~2.0 Osm/L, and typically at least ~2.25 Osm/L. Compositions with tonicities of ~2.5, ~2.75, ~3.0, ~3.25, ~3.5, ~3.75 or even ~4 Osm/L can be used. Cationic surfactants again are preferred, preferably at levels of ~0.5 to ~2 g/L, more preferably of ~0.7 to ~1.8 g/L, and most preferably of ~0.8 to ~1.5 g/L.

For devices not yet in contact with body tissue, the conditions can be more extreme, i.e., higher toxicity and very high osmolarity. In either case, the application of the antimicrobial composition can be by rinsing, wiping, flushing, etc., optionally in conjunction with scraping/debridement and optionally followed by a rinsing step. In extreme cases, the implanted article can be removed and treated ex vivo with the composition prior to re-implantation.

Alternative or additional techniques involve preparing a body area in which an implant is to be inserted by washing, wiping and/or irrigating that area with an antimicrobial composition. This can be done in conjunction with surgical preparation sterilization with the same or similar composition.

While various embodiments of the present invention have been provided, they are presented by way of example and not limitation. To the extent feasible, as long as they are not interfering or incompatible, features and embodiments described above in isolation can be combined with other features and embodiments.

That which is claimed is:

1. A process for reducing bacterial colonization in or around the area of a wound, said process comprising applying to said area a gel that comprises at least one PEG and an aqueous composition having a pH of from 2 to 4, a total solute concentration of from 1.8 to 4.0 Osm/L, and from 0.9 to 1.7 g/L of at least one cationic surfactant, said gel being free of sporicides, antifungals and antibiotics.

2. The process of claim 1 wherein said aqueous composition has a total solute concentration of from 1.8 to 2.8 Osm/L.

3. The process of claim 1 wherein said at least one cationic surfactant comprises benzalkonium chloride.

4. The process of claim 1 wherein said at least one cationic surfactant is benzalkonium chloride.

5. A process for reducing bacterial colonization in or around the area of a wound, said process comprising applying to said area a gel that consists essentially of at least one PEG, an aqueous composition having a pH of from 2 to 4, a total solute concentration of from 1.8 to 4.0 Osm/L, and from 0.9 to 1.7 g/L of at least one cationic surfactant, and optionally one or more of an emollient, a lotion, a humectant, a glycosaminoglycan, an analgesic, colloidal silver and a coalescent.

6. The process of claim 5 wherein said aqueous composition has a total solute concentration of from 1.8 to 2.8 Osm/L.

7. The process of claim 5 wherein said at least one cationic surfactant comprises benzalkonium chloride.

8. The process of claim 5 wherein said at least one cationic surfactant is benzalkonium chloride.

9. A process for reducing bacterial colonization in or around the area of a wound, said process comprising applying to said area a gel that comprises
   a) at least one PEG and
   b) a composition having a pH of from 2 to 4 and a total solute concentration of from 1.8 to 4.0 Osm/L that consists essentially of
      (1) water,
      (2) a buffer system that comprises of one or more organic acids and at least one salt of one or more organic acids, and
      (3) from 0.9 to 1.7 g/L of at least one cationic surfactant,
   said gel being free of materials having antimicrobial properties other than those provided by said composition.

10. The process of claim 9 wherein said composition has a total solute concentration of from 1.8 to 2.8 Osm/L.

11. The process of claim 9 wherein said at least one cationic surfactant comprises benzalkonium chloride.

12. The process of claim 9 wherein said at least one cationic surfactant is benzalkonium chloride.

13. The process of claim 9 wherein said one or more organic acids comprise at least one polyacid.

14. The process of claim 13 wherein said at least one polyacid comprises citric acid.

15. The process of claim 14 wherein said at least one salt of one or more organic acids comprises a salt of a polyacid.

16. The process of claim 9 wherein each of said one or more organic acids is a polyacid.

17. The process of claim 9 wherein said one or more organic acids is citric acid.

18. The process of claim 17 wherein said at least one salt comprises a salt of citric acid.

19. The process of claim 9 wherein said at least one salt is a salt of citric acid.

20. The process of claim 9 wherein said one or more organic acids is acetic acid.

* * * * *